US00PP08948P

United States Patent [19]

Bradford et al.

[11] Patent Number: Plant 8,948

[45] Date of Patent: Oct. 18, 1994

[54] NECTARINE TREE (DIAMOND RAY)

[76] Inventors: Lowell G. Bradford, 12439 E. Savana Rd.; Norman G. Bradford, 11875 E. Savana Rd., both of Le Grand, Calif. 95333

[21] Appl. No.: 183,351

[22] Filed: Jan. 19, 1994

[51] Int. Cl.[5] ..... A01H 5/00

[52] U.S. Cl. ..... Plt./41.1

[58] Field of Search ..... Plt. 41.1

*Primary Examiner*—James R. Feyrer

[57] ABSTRACT

The present invention relates to a nectarine tree and more particularly to a new and distinct variety broadly characterized by a large size, vigorous, hardy, productive and regular bearing tree. The fruit matures under the ecological conditions described approximately the first week in July, with first picking on Jul. 1, 1983. The fruit is uniformly large in size, excellent in flavor, attractively globose in shape, clingstone in type, very firm in texture, and full red in skin color. The variety was developed as a hybridized seedling from Red Diamond (U.S. Plant Pat. No. 3,165), as the selected seed parent, and an unnamed seedling as the selected pollen parent.

1 Drawing Sheet

BACKGROUND OF THE VARIETY

In a continuing effort to improve the quality of shipping fruits, we, the inventors, typically hybridize a large number of nectarine, peach, plum, apricot, and cherry seedlings each year. The present invention relates to a new and distinct variety of nectarine tree, which has been denominated varietally as "Diamond Ray". The present variety was hybridized by us in 1986, and the resulting seedling was planted in a cultivated area of our experimental orchard at Bradford Farms near Le Grand, Calif. in Merced County (San Joaquin Valley). Specifically, the hybridized seedling was originated by using Red Diamond (U.S. Plant Pat. No. 3,165) as the selected seed parent and an unnamed seedling as the selected pollen parent. Subsequent to origination of the present variety of nectarine tree, we asexually reproduced it by budding and grafting, and such reproduction of plant and fruit characteristics were true to the original plant in all respects.

The present variety most nearly resembles the Summer Bright (U.S. Plant Pat. No. 7,049) by producing fruit that is full red in skin color, sweet and flavorful in taste, clingstone in type, and extremely firm in texture, but is distinguished therefrom and an improvement thereon by producing fruit that ripens approximately twelve days earlier and has substantially less red streaking in the flesh.

The present variety is similar to its selected seed parent, Red Diamond (U.S. Plant Pat. No. 3,165), in fruit appearance by being a full red colored nectarine with excellent firmness, but is distinguished therefrom by ripening seven days later and by being a clingstone instead of a freestone.

DRAWING

The accompanying photograph exhibits four whole fruits positioned to display the characteristics of the skin color and form, a sectioned half fruit divided transverse to the suture plane to reveal the flesh and stone, and representative leaves.

POMOLOGICAL CHARACTERISTICS

Referring now more specifically to the pomological characteristics of this new and distinct variety of nectarine tree, the following has been observed under the ecological conditions prevailing near Le Grand, Merced County (San Joaquin Valley), Calif., and was developed at the state of hard eating ripe on Jul. 7, 1993. All major color code designations are by reference to the Inter-Society Color Council, National Bureau of Standards. Common color names are also used occasionally.

TREE

Size: Large.
Vigor: Vigorous.
Growth: Spreading and dense.
Form: Vase formed.
Hardiness: Hardy.
Production: Very productive.
Bearing: Regular bearer.
Trunk:
- *Size.*—Medium.
- *Texture.*—Medium.
- *Bark Color.*—Brownish gray [64. brGy].
- *Lenticels.*—Numerous. Color: Light brown [57. 1.Br]. Average size: ¼" [6.4 mm.].

Branches:
- *Size.*—Medium.
- *Texture.*—Medium.
- *Color.*—1st Year Wood Topside: Light grayish red [18. 1.gy.R]. 1st Year Wood Underside: Brilliant yellow green [116. brill.YG]. Older Wood: Grayish brown [61. gy.Br].
- *Lenticels.*—Numerous, small.

Leaves:
- *Size.*—Large. Average length: 5¾" [146.1 mm.]. Average width: 1 11/16" [42.9 mm.].
- *Thickness.*—Medium.
- *Form.*—Elliptical.
- *Apex.*—Acuminate.
- *Base.*—Acute.
- *Surface.*—Smooth.
- *Color.*—Dorsal Surface: Moderate olive green [125. m.OlG]. Ventral Surface: Moderate yellow green [120. m.YG].
- *Margin.*—Finely serrate.
- *Venation.*—Pinnately net veined.

*Petiole.*—Average length: ⅜" [9.5 mm.]. Average thickness: 1/16" [1.6 mm.]. Color: Moderate yellow green [120. m.YG].

*Stipules.*—Numerous. Average length: 5/32" 4.0 mm.].

*Glands.*—Average number: Mostly 2 per leaf. Position: Mostly oppositely positioned on petiole and base of blade. Size: Medium. Form: Reniform. Color: Brilliant yellow green [116. brill.YG].

Flower buds:

*Hardiness.*—Hardy.

*Size.*—Medium.

*Length.*—Medium.

*Form.*—Free.

*Surface.*—Pubescent.

Flowers:

*Blooming period.*—Medium as compared with other varieties.

*Size.*—Large.

*Color.*—Light pink [4. 1.Pk].

FRUIT

Maturity when described: Hard but eating ripe, Jul. 7, 1993.

Date of first picking: Jul. 1, 1993.

Date of last picking: Jul. 13, 1993.

Size: Uniform, large.

*Average diameter axially.*—2⅝" [66.7 mm.].

*Average transversely in suture plane.*—2⅞" [73.0 mm.].

Form: Uniform, symmetrical, globose, but compressed transversely.

*Longitudinal section form.*—Round.

*Transverse section through diameter.*—Round with slight protrusions along suture.

Suture: An inconspicuous shallow line extending from the base to slightly beyond the apex, with a slight depression on both sides of the pistil point.

Ventral surface: Rounded, lipped on both sides toward the apex.

Lips: Slightly unequal.

Cavity: Flaring, circular, suture showing on both sides.

*Depth.*—½" [12.7 mm.].

*Breadth.*—1" [25.4 mm.].

Base: Truncate.

Apex: Rounded.

Pistil point: Negligible in length, completely depressed within the suture.

Stem: Medium.

*Average length.*—⅜" [9.5 mm.].

*Average width.*—3/16" [4.8 mm.].

Skin:

*Thickness.*—Medium.

*Texture.*—Medium.

*Tenacity.*—Tenacious to flesh.

*Tendency to crack.*—None observed as of yet.

*Color.*—Moderate red [15. m.R] to very deep red [14. v.deep R] over the entire surface with some brilliant orange yellow [67. brill.OY] freckling, mostly towards the apex.

Flesh:

*Color.*—Brilliant yellow [83. brill.Y] with very little moderate red [15. m.R] flecking.

*Amygdalin.*—Scarce.

*Juice.*—Abundant, rich.

*Texture.*—Very firm, crisp.

*Fibers.*—Abundant, fine, tender.

*Ripens.*—Evenly.

*Flavor.*—Sweet, with moderate acid.

*Aroma.*—Moderate.

*Eating quality.*—Very best.

STONE

Type: Clingstone.

Form: Oval.

Base: Straight.

Apex: Acute.

Sides: Equal.

Surface: Irregularly furrowed toward the apex and pitted toward the base.

Ridges: Jagged toward the base.

Color: Strong brown [55. s.Br].

Pit wall: 7/32" [5.6 mm.] thick.

Tendency to split: Very slight.

Kernel:

*Form.*—Oval.

*Taste.*—Sweet.

*Viable.*—Yes.

*Average width.*—½" [12.7 mm.].

*Average length.*—¾" [19.1 mm.].

*Color.*—Brilliant yellow [83. brill.Y] when first cracked.

*Pellicle color.*—Grayish yellow [90. gy.Y].

*Amygdalin.*—Abundant.

USE

Market: Fresh and long distance shipping.

Keeping quality: Excellent.

Shipping quality: Excellent.

Resistance to insects: No unusual susceptibilities noted.

Resistance to diseases: No unusual susceptibilities noted.

Although the new variety of nectarine tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

We claim:

1. A new and distinct variety of nectarine tree, substantially as illustrated and described, which is most similar to the Summer Bright nectarine (U.S. Plant Pat. No. 7,049), by producing clingstone fruit that is full red in skin color, sweet and flavorful in taste, and extremely firm in texture, but is distinguished therefrom and an improvement thereon by having a large blossom instead of small and by producing fruit that ripens approximately twelve days earlier and has substantially less red streaking in the flesh.

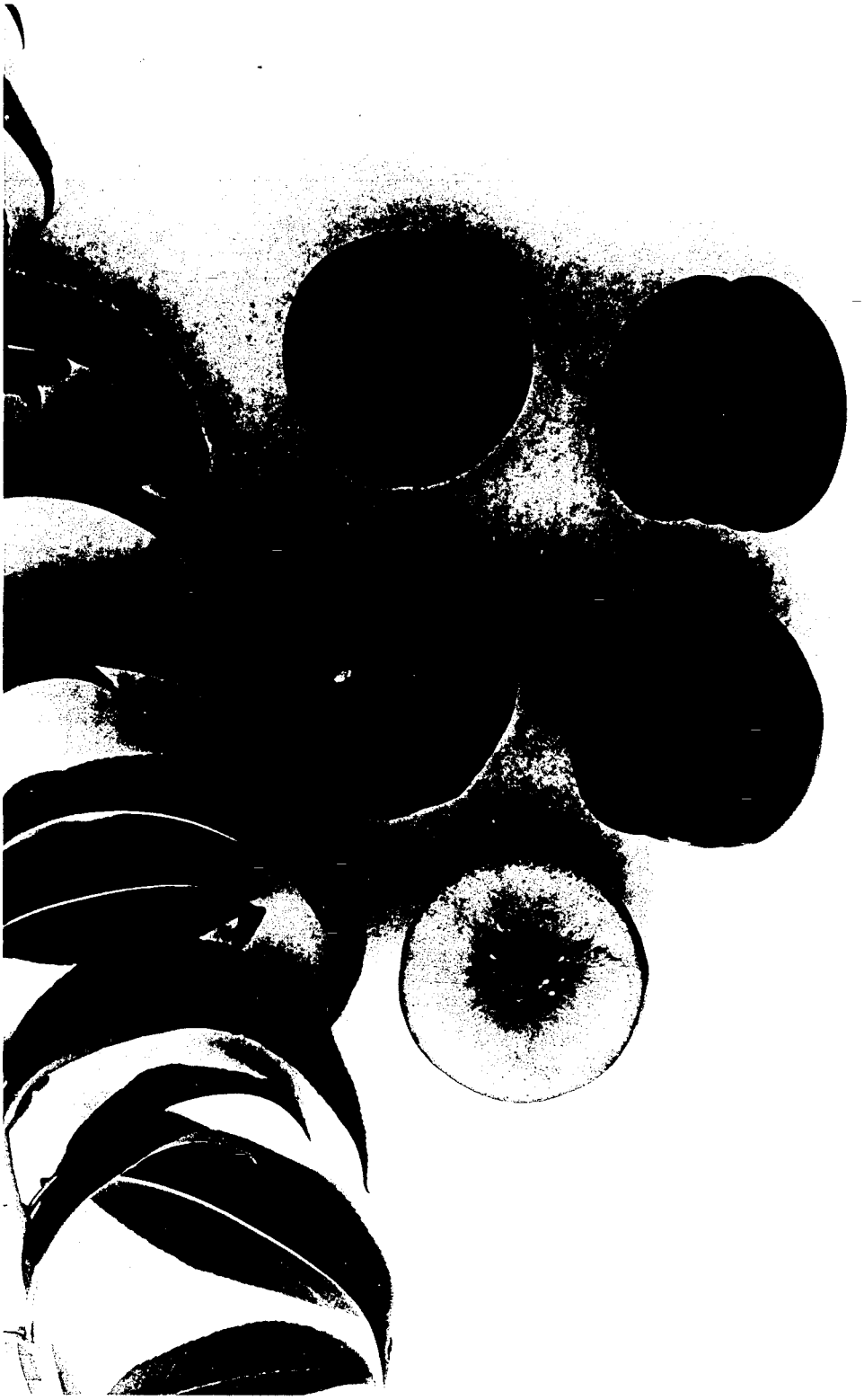

* * * * *